(12) United States Patent
Burke

(10) Patent No.: US 10,223,877 B2
(45) Date of Patent: Mar. 5, 2019

(54) VISUAL CHARACTERISTIC-OF-INTEREST POSITION INDICATOR FOR MACHINE CONVEYABLE MATERIAL

(71) Applicant: John Burke, Tampa, FL (US)

(72) Inventor: John Burke, Tampa, FL (US)

( * ) Notice: Subject to any disclaimer, the term of this patent is extended or adjusted under 35 U.S.C. 154(b) by 0 days.

(21) Appl. No.: 15/271,690

(22) Filed: Sep. 21, 2016

(65) Prior Publication Data

US 2018/0082551 A1    Mar. 22, 2018

(51) Int. Cl.
| | | |
|---|---|---|
| *G08B 3/00* | (2006.01) | |
| *G08B 5/00* | (2006.01) | |
| *G08B 7/00* | (2006.01) | |
| *G08B 5/36* | (2006.01) | |
| *G01N 21/89* | (2006.01) | |

(52) U.S. Cl.
CPC ........... *G08B 5/36* (2013.01); *G01N 21/8901* (2013.01)

(58) Field of Classification Search
CPC ....... G08B 5/36; B65H 43/04; G01N 21/8901
See application file for complete search history.

(56) References Cited

U.S. PATENT DOCUMENTS

| | | | | |
|---|---|---|---|---|
| 3,958,078 A * | 5/1976 | Fowler | ................. | G01N 23/043 348/127 |
| 5,659,624 A * | 8/1997 | Fazzari | ................. | B07C 5/3422 209/580 |
| 6,626,557 B1 | 9/2003 | Taylor | | |
| 6,993,404 B2 | 1/2006 | Lev-Ami | | |
| 7,656,520 B2 * | 2/2010 | Cohn | .................... | B07C 5/3427 209/581 |
| 8,086,156 B2 * | 12/2011 | Tao | ..................... | G03G 15/5058 198/806 |
| 8,436,741 B2 | 5/2013 | Krapf | | |
| 8,687,060 B1 * | 4/2014 | Wolff | .................. | G06F 3/03543 250/206.2 |
| 2003/0231317 A1 * | 12/2003 | Sepulveda Carlos | .... | G01K 1/16 356/614 |
| 2005/0051528 A1 * | 3/2005 | Chen | ........................ | A21B 3/07 219/388 |
| 2006/0164647 A1 * | 7/2006 | Shibata | .................. | G01N 21/89 356/430 |
| 2008/0204733 A1 * | 8/2008 | Jones | ..................... | G01N 21/21 356/237.1 |
| 2008/0270324 A1 * | 10/2008 | Allard | ..................... | A47F 10/06 705/400 |
| 2009/0159175 A1 * | 6/2009 | Nakahira | ................ | B32B 41/00 156/64 |
| 2010/0039510 A1 * | 2/2010 | Gold | .................. | G06Q 30/0603 348/92 |
| 2010/0123597 A1 * | 5/2010 | Kitsukawa | ............ | G06F 1/1626 345/173 |
| 2011/0086193 A1 * | 4/2011 | Nakazono | ............... | B32B 37/22 428/41.8 |
| 2013/0170734 A1 * | 7/2013 | Uchiyama | ................ | G06K 9/46 382/149 |
| 2013/0177232 A1 * | 7/2013 | Hirano | .................. | G06T 7/0004 382/141 |
| 2015/0061884 A1 * | 3/2015 | Hwang | .............. | H04N 21/4126 340/815.45 |
| 2015/0133229 A1 * | 5/2015 | Weston | .................. | A63G 21/18 472/117 |

* cited by examiner

*Primary Examiner* — Quang Pham

(57) ABSTRACT

A system that visually indicates the position of a characteristic-of-interest of a machine conveyable material. The visual indication comprising direct, indirect and combinations thereof.

16 Claims, 4 Drawing Sheets

VISUAL CHARACTERISTIC-OF-INTEREST POSITION INDICATOR FOR MACHINE CONVEYABLE MATERIAL

CROSS-REFERENCE TO RELATED APPLICATIONS

None

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

The invention relates to the inspection of material which is capable of being conveyed on a machine for conveying such material. The conveying machines often have a bed track along which the material travels. Others utilize some other support for the material. One of the other types of machines uses chains with clips that support and transport the material. The preceding are examples of machines and are not intended to be limiting in any way. The invention is applicable to a wide variety of materials capable of being conveyed on machines. Said machines may be manual, automated and both. The invention also relates to the off-line (i.e. off the machine) inspection of material capable of being conveyed by a machine. Off line or off machine material inspection is typically done on a test fixture designed to accommodate the material to be inspected. The invention is capable of accommodating a variety of off line inspection setups and is not limited to specific ones.

Material, as used here, is to be interpreted in the broadest possible sense. The material need not be continuous along the length or width. The thickness of the material is likewise not important and may be of any thickness suitable for its application. Examples of conveyed material forms include, but are not limited to, films, sheets and bars. The invention is applicable regardless of the physical form of the material.

The material may be comprised of any composition capable of being conveyed on a machine. Examples include, but are not limited to, metals such as aluminum or steel, a variety of plastics and combinations thereof. Other materials and combinations of materials are also possible. The material itself may be flat, formed and a combination thereof. The preceding are examples and are not intended to be limiting in any way. The invention is applicable regardless of the material type, shape or composition.

Generally, the invention is applicable to any device or devices which inspect the material. Inspect here is meant in the broadest sense and may comprise inspecting the material for any characteristic or multiple characteristics-of-interest as desired by the application. A couple of examples of such devices are vision systems and pinhole detectors. The invention is applicable regardless of type of inspection device. The inspection device serves as the characteristic-of-interest detection and location information source.

Background Art

Various devices inspect material for a particular characteristic-of-interest or multiple characteristics-of-interest. Examples of characteristic-of-interest comprise color, transparency, thickness, formed features, bar codes, labels, defects and combinations thereof. They also comprise items added to or into the material, for example bar codes, labels and various products. A characteristic-of-interest may comprise multiple instances and combinations. These examples are not intended to be limiting in any sense. The invention is applicable regardless of the nature of the characteristic-of-interest.

Existing inspection devices generally indicate the presence or lack of presence of a characteristic-of-interest either by indication on a local HMI (Human Machine Interface) or transmitting said indication to a remote HMI. It is possible for a device to do both. Remote HMI here is intended to indicate it is not an integral part of the device and does not imply information about the distance or nature. In some cases the characteristic-of-interest information is formatted and displayed on the local or remote HMI so as to indicate a relative position. A HMI may comprise a variety of forms including a simple panel with indicators to graphic displays. HMIs may comprise such devices as a computer or PLC (Programmable Logic Controller). This description of HMI is not intended to be limiting.

BRIEF SUMMARY OF THE INVENTION

The invention provides visual indication of the position of the material characteristic-of-interest at or in proximity to the position of said characteristic-of-interest. The visual position information is particularly useful for personnel trying to determine the cause of the characteristic-of-interest presence or absence. Examples of such causes include, but are not limited to, defective machine parts damaging the material, incorrectly operating equipment and material defects. The position of the characteristic-of-interest often provides a clue to the source of it. The position of the characteristic-of-interest may also be useful for determining if the material or portion of material should be rejected or otherwise processed. Another aspect of the characteristic-of-interest indication could be to confirm the presence of a desired characteristic-of-interest.

In various embodiments it may be preferred to have the visual indicator located above, below or both above and below the material under inspection and generally perpendicular to the direction of travel of the material. The visual indicator would then indicate the characteristic-of-interest position. The preceding embodiment would typically be utilized when the material is not visible to personnel during the inspection by a device, although that need not be the case. The visual indication would then be activated when the characteristic-of-interest aligns with it. This embodiment class is here termed indirect indication.

In another embodiment the visual indication utilizes a visual indicator that illuminates an area of the material at or in proximity to the characteristic of interest. That embodiment would typically be utilized when the material is visible to personnel during the inspection by a device. Configurations that utilize illumination of the characteristic-of-interest on the material are here termed direct indication.

A third embodiment combines the direct and indirect indications described previously. It offers the indication methods of both types in one embodiment.

Indirect indication comprises a visual indicator or multiple indicators arranged essentially perpendicular to the direction of travel of the material and above said material so that the illuminated indicator corresponds to or is in proximity to the characteristic of interest. The relative size and resolution of the indicators as compared to the characteristic-of-interest of the material may vary greatly and is dependent largely on the needs of the application. There is not a necessary or inherent relative size or resolution in the invention. The indicator may be comprised of any suitable means of generating visible light and may take a variety of forms including, but not limited to, LED or LEDs, LASER or LASERs, incandescent, fluorescent and combinations thereof. Said visible light may also be generated as a fluorescence or phosphorescence from light emitted by various devices. The indicators may also take the form light manipulating devices such as LCDs or mirroring devices. These examples are some possible indicator embodiments and are not intended as limiting.

A variant of the configuration is that the indicator device would be located below the material under inspection. Yet another variant of the configuration would have an indicator device arrangement above and below the material under inspection.

In the embodiment of direct indication, the illumination of the characteristic-of-interest may be comprised of any suitable means of causing visible light at or in proximity to the position of the characteristic of interest. The light may be emitted from a variety of light emitting devices including, but not limited to, LED or LEDs, LASER or LASERs, incandescent, fluorescent and combinations thereof. The light may also be generated as a fluorescence or phosphorescence from light emitted by various devices. Some materials may also be illuminated via fluorescence or phosphorescence of the material from a non-visible light source or sources.

The combined direct and indirect indicator embodiment may utilize the illumination methods and devices described previously in various combinations. Alternatively, the same illumination source could perform both direct and indirect indication by utilizing one or more optical devices to separate the illumination source light into the direct and indirect components.

In one embodiment, the indicator device is a so called stand-alone device, meaning it is not part of another device. In another embodiment it is incorporated into another device. Both embodiments are equivalent in regard to the function of the invention.

Various forms of the indicators illumination are possible. One is that all are normally not illuminated and only illuminated to indicate the position of the characteristic of interest. Conversely all could normally be illuminated and not illuminated to indicate the position of the characteristic of interest. Another variant would be the illumination flashing on and off. These forms are collectively termed on-off indication.

Another form of the indicators illumination utilizes illumination colors to indicate the position of the characteristic of interest. One embodiment would have all the indicators illuminated green and change to red to indicate the position of the characteristic of interest. Multiple indicator colors could be used in a variety of ways including, but not limited to, encoding the position of the characteristic-of-interest and signaling an indicator being disabled. The preceding example is for illustrative purposes and is not intended to be limiting. A plethora of color combinations could be utilized to perform the indicator illumination function.

Combining on-off and color indicators is another possible embodiment.

In the following section indirect, direct and combination indirect and direct illumination embodiment embodiments are explained in detail. The invention is not intended to be limited in its application to the details of construction and to the arrangements of the components described in the following description or illustrated in the drawings. The invention is capable of other embodiments and of being practiced and carried out in various ways.

The phraseology and terminology employed herein are for the purpose of description and should not be regarded as limiting.

It is the intention of the invention to provide a visual indication of the position of a characteristic-of-interest of a material and may be utilized with a plethora of devices used with machines that convey material manually, automatically and both. The invention provides position information regarding a characteristic-of-interest of a conveyed material in a form not previously available and which is not anticipated, rendered obvious, suggested, or even implied by any of the prior art, either alone or in any combination.

BRIEF DESCRIPTION OF THE DRAWINGS

The following drawings illustrate the best modes presently contemplated for carrying out the present invention (Preferred Embodiment).

The direct, indirect and combined direct and indirect indicator illumination configurations are illustrated.

DETAILED DESCRIPTION OF THE INVENTION

Principle of Operation

Various devices inspect material for characteristics-of-interest. Upon detection of said characteristic-of-interest or multiple characteristics-of-interest, an indication of the event is generated. The indication may be to alert personnel and/or an automated controller. One example of a personnel alert device is an indicator illuminating on the HMI of the device. Another might be an audio alarm. The alert to the automated controller is normally electronic and may take multiple forms—discrete signal lines or communication networks among them. These forms of alerts may provide indication of a characteristic-of-interest has been detected, but do not provide immediate visual information regarding the position of the characteristic on the material under inspection to an observer of said material.

The invention utilizes characteristic-of-interest position information from inspection devices capable of providing such position information to indicate said characteristic by direct illumination, indirect illumination and combination direct and indirect illumination.

Refer to FIGS. 1, 2, 3 and 4 for the following description.

The Components:

The preferred embodiments comprise one or more visual indicators that provide direct illumination, indirect illumination or combination direct and indirect illumination. The illumination indicates the position of the characteristic(s) of interest relative to the material under inspection.

Figure 1:
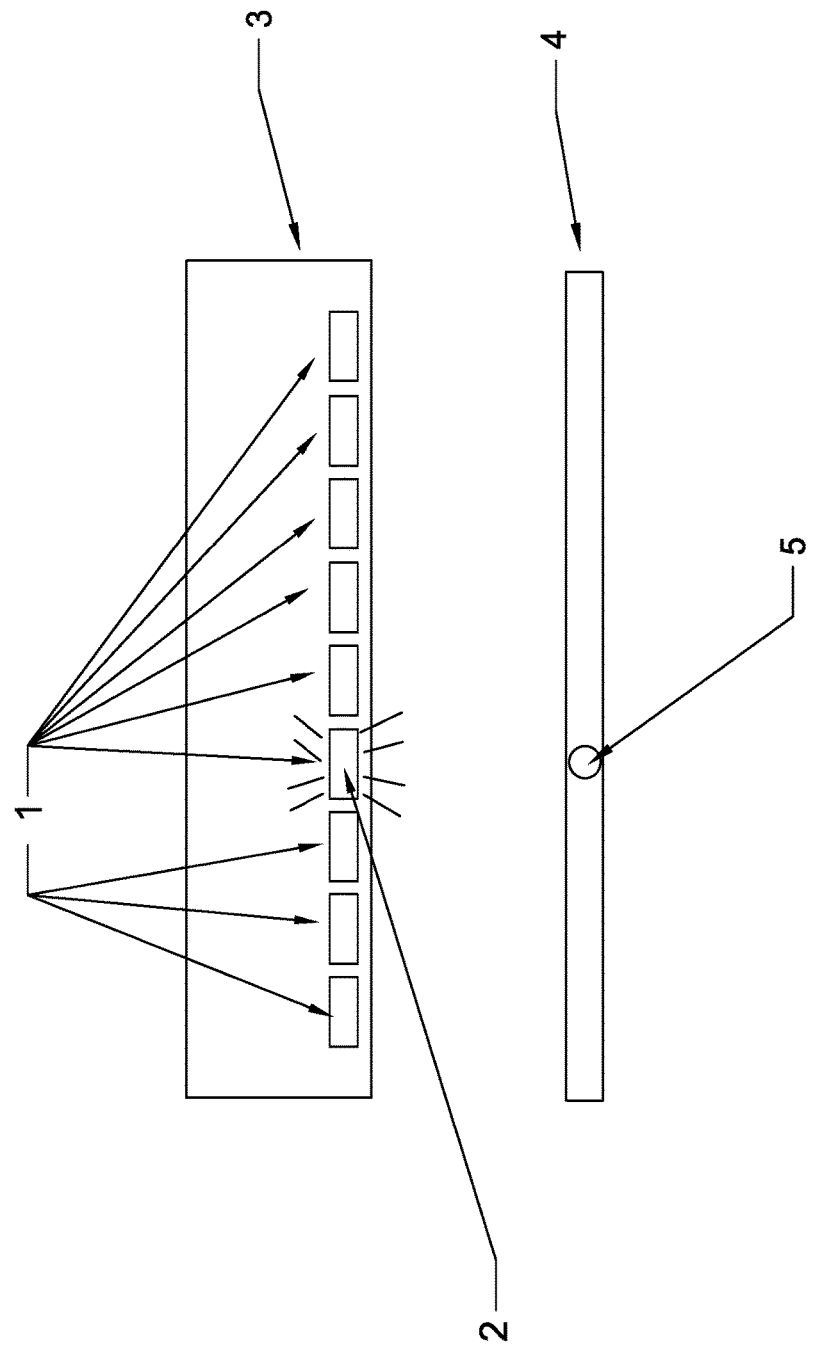
FIG. 1 Component View of the Indirect Illumination Configuration.

For the indirect illumination preferred embodiment of FIG. 1, one or more visual indicators 1, are located in or on an structure 3 and across the width of the structure, where such structure 3 essentially spans the width of the material under inspection 4. The visual indicators 1, are visible to an observer when illuminated. The illumination of the visual indicators 1 allows indication of the position of a characteristic-of-interest on the material under inspection. FIG. 1 illustrates a configuration where the visual indicators 1 are located above the material under inspection 4 in or on a structure 3 where the visual indicators are able to emit light that is visible to an observer. The active indicator 2 is indicating the position of the characteristic-of-interest 5 on the material under inspection 4. FIG. 1 illustrates the on-off configuration as well as the color configuration as the indicators 1 could all be off (or all on) or all a particular color, e.g. green, and the active indicator 2 could be on (or off) or a different color, e.g. red.

A variant of the indirect illumination preferred embodiment of FIG. 1 is that an additional color of illumination for the indicators 1 could be utilized to indicate an area of the material not being inspected. Flashing indicator(s) 1 could also be utilized for the same purpose.

Figure 2:
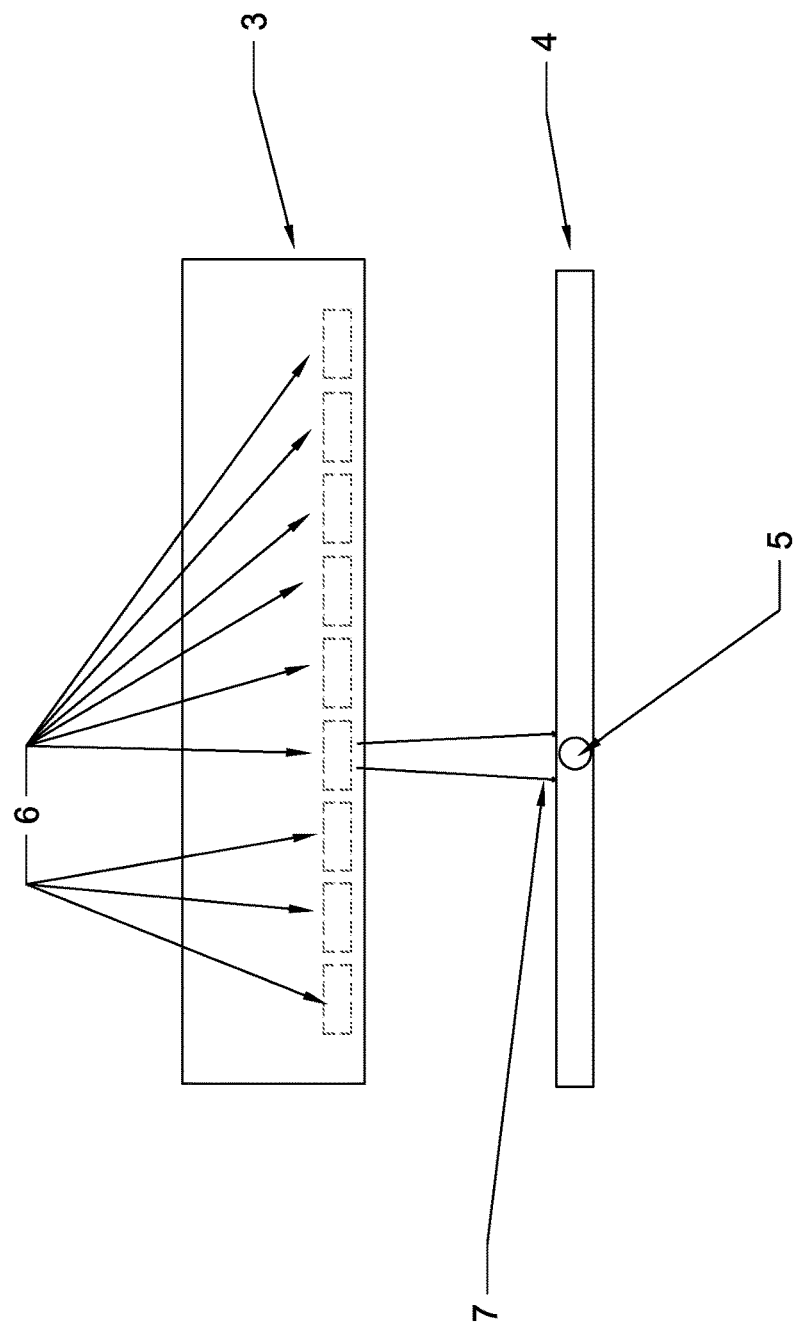
FIG. 2 Component View of the Direct Illumination Configuration

For the direct illumination preferred embodiment of FIG. 2, one or more visual indicators 6, shown as hidden (dashed lines) in the view as they are typically within the structure 3 and not directly visible, are located in or on an structure 3 and across the width of said structure. The structure 3 essentially spans the width of the material under inspection 4 and the visual indicators are configured so as to be capable of illuminating 7 the material under inspection 4 so as to indicate the position of a characteristic-of-interest. The direct embodiment FIG. 2 differs from the indirect embodiment FIG. 1 in that the projected light in FIG. 2 is visible directly 7 on the material under inspection 4 so as to indicate the position. FIG. 2 illustrates the on-off configuration as well as the color configuration as the indicators 6 could all be off (or on) or all a particular color, e.g. green, and the active indication 7 could be on (or off) or a different color, e.g. red.

A variant of the direct illumination preferred embodiment of FIG. 2 is that an additional color of illumination for the indicators 6 could be utilized to indicate an area of the material not being inspected. Flashing indicator(s) 6 could also be utilized for the same purpose.

Figure 4:
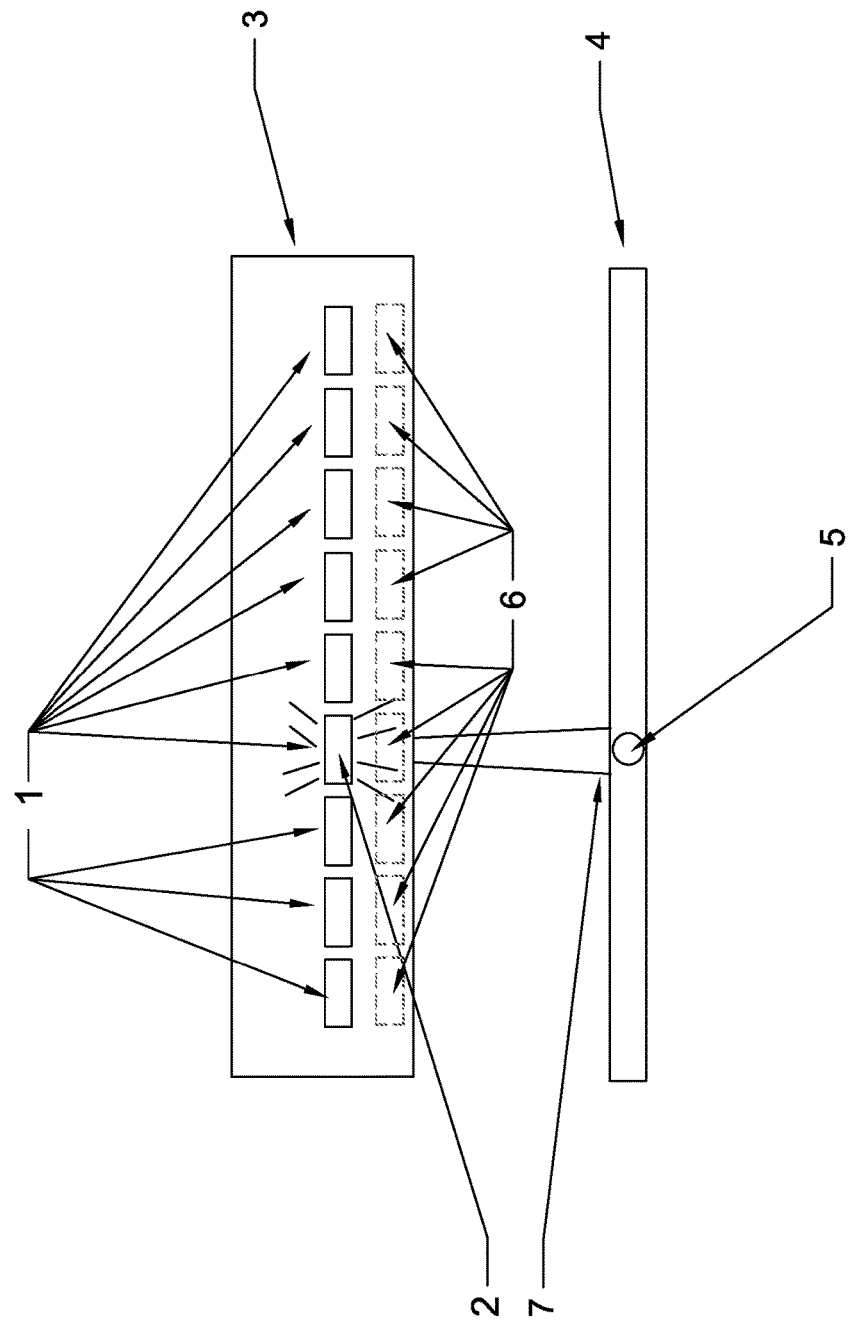
FIG. 4 Component View of Combined Indirect and Direct Illumination Configuration

In the combination indirect and direct illumination embodiment of FIG. 4, one or more indirect visual indicators 1 and direct visual indicators 6 are located in or on an structure 3 and across the width of the structure, where such structure 3 essentially spans the width of the material under inspection 4. Although this description depicts separate indirect 1 and direct 6 visual indicators, the function of both could be combined in one visual indicator device. The one light source variant might utilize an optical component that splits the light into different directions so as to form the direct and indirect indicators. The description and function would otherwise be unchanged. The indirect visual indicator 2 illumination is visible on the structure and corresponds to the location of the characteristic-of-interest 5. The direct visual indicator projection 7 illuminates the location of the characteristic-of-interest 5 on the material under inspection 4. FIG. 4 illustrates the on-off configuration as well as the color configuration as the indicators 1 and 6 could all be off (or all on) or all a particular color, e.g. green, and the active indication 2 and 7 could be on or a different color, e.g. red.

A variant of the indirect and direct illumination embodiment of FIG. 4 is that an additional color of illumination for the indicators 1 and 6 could be utilized to indicate an area of the material not being inspected. Flashing indicator(s) 1 and 6 could also be utilized for the same purpose.

The visual indicators of the preferred embodiments 1 FIG. 1, 6 FIGS. 2 and 1, 6 of FIG. 4 may be comprised of any light emitting device(s) suitable for the invention. For purposes of illustration, LEDs are used. Said visible light may also be generated by a plethora of sources as described previously.

Those skilled in the art will recognize that many means are possible to illuminate the LEDs or other light emitting devices that form the indicators. For purposes of illustration, one possible circuit is described. It is not intended to be limiting in any sense.

Figure 3:
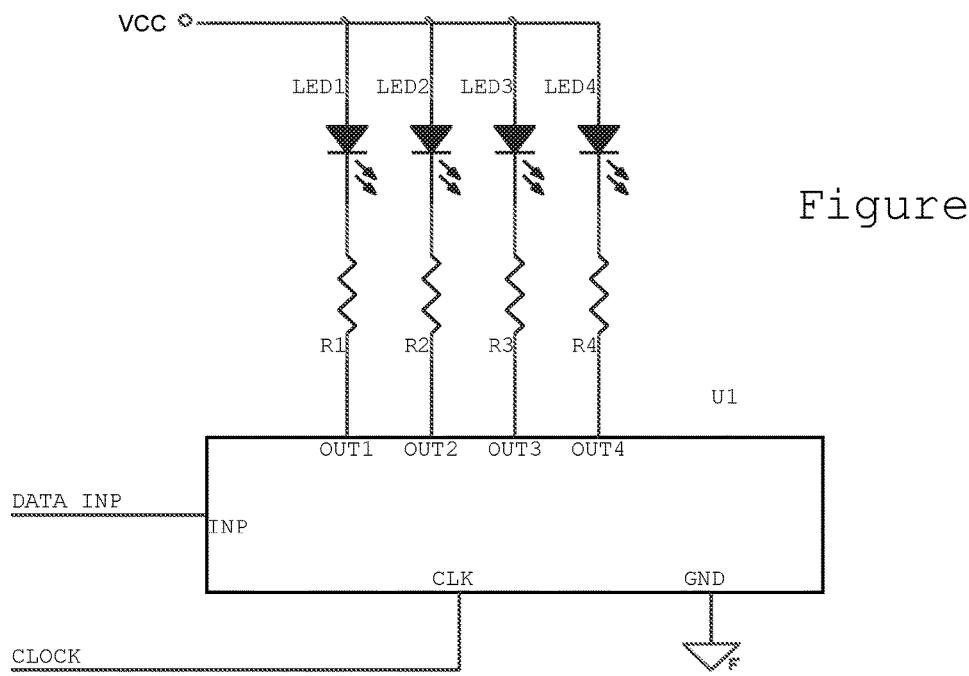
FIG. 3 Visual Indicator Drive Circuit Example

Referring to FIG. 3, the IC U1 is a 4 bit shift register of generic type. It is of the 74HCxx logic technology. It is driven by an external synchronous serial source comprising serial data DATA INP, which drives INP of U1 and serial clock CLOCK, which drives CLK of U1. The external source DATA INP data consists of logic 1 or 0 and thereby controls illumination of the LEDs. In the circuit configuration shown, a logic 0 illuminates the LED indicator and a logic 1 does not. When an output of U1-OUT1, OUT2, OUT3, OUT4—is set to logic 0, the voltage sourced by VCC is impressed across the corresponding LED1, LED2, LED3, LED4 and the resistors R1, R2, R3 and R4 limit the current through the corresponding LEDs. The current flowing through the LEDs causes them to be illuminated.

Note that there is no requirement that the circuit that illuminates the LEDs or any other light emitting device, be physically located in proximity to the LEDs or other light emitting devices.

The invention claimed is:

1. A visual indirect material defect position indication system for conveyed material inspection, comprising:
   one or more visual indicators, said one or more visual indicators comprising one or more light sources;
   one or more material inspection devices designed to inspect machine conveyed material on a structure for defect position information of said machine conveyed material and actuate the correlated visual indicator of the one or more visual indicators with a position of a defect of the machine conveyed material based on the detect position information, said one or more material inspection devices designed to inspect for defects in said machine conveyed material, said machine conveyed material comprising formed, flat and combinations thereof of foil, film, sheet, and combinations thereof;
   said structure designed to span the width of and position the one or more visual indicators in proximity to the machine conveyed material under inspection, said one or more visual indicators arranged across the structure so that said correlated visual indicator of said one or more visual indicators is operable to actuate to indicate the position of the defect in the machine conveyed material under inspection;
   the one or more visual indicators actuate by illuminating, not illuminating and combinations thereof;
   wherein the one or more visual indicators comprise being normally illuminated and the correlated visual indicator being turned off or flashed when the defect of said machine conveyed material is detected at the position of the correlated visual indicator, or alternatively wherein the one or more visual indicators comprise being normally off and the correlated visual indicator being illuminated or flashed when the defect of said machine conveyed material is detected at the position of the correlated visual indicator.

2. The visual indirect material defect position indication system for conveyed material inspection in claim 1, wherein said one or more material inspection devices comprise a pinhole detector, a machine vision and combinations thereof wherein said one or more visual indicators are incorporated into said one or more material inspection devices.

3. The visual indirect material defect position indication system for conveyed material inspection in claim 1, wherein the one or more visual indicators comprise being one color when the defect is not detected and changing to a different color when the defect is detected at the position of the correlated visual indicator.

4. The visual indirect material defect position indication system for conveyed material inspection in claim 1, wherein the one or more visual indicators comprise a different color, colors, flashing and combinations thereof to indicate an area of the machine conveyed material not monitored for defects.

5. The visual indirect material defect position indication system for conveyed material inspection in claim 1, wherein the one or more visual indicators are comprised of one or more LED, LASER, incandescent, fluorescent and combinations thereof light emitting devices.

6. A visual direct material defect position indication system for conveyed material inspection, comprising:
  one or more visual indicators, said one or more visual indicators comprising one or more light sources;
  one or more material inspection devices designed to inspect machine conveyed material a structure for defect position information of said machine conveyed material and actuate the correlated visual indicator of said machine conveyed material indicators with a position of a defect of the machine conveyed material based on the detect position information, said one or more material inspection devices designed to inspect for defects in said machine conveyed material, said machine conveyable material comprising formed, flat and combinations thereof of foil film, sheet and combinations thereof;
  said structure designed to span the width of and to position the one or more visual indicators in proximity to the machine conveyed material under inspection, the position of each visual indicator of the one or more visual indicators designed to correlate a projection of the visual indicator light onto the machine conveyed material under inspection with the position of a defect in the machine conveyed material under inspection;
  the one or more visual indicators actuation comprising illuminating, not illuminating and combinations thereof an area of the machine conveyed material under inspection;
  wherein the one or more visual indicators comprise normally illuminating the machine conveyed material under inspection and not illuminating or flashing an area of the machine conveyed material under inspection when the defect is detected at the indicator position, or alternatively wherein the one or more visual indicators comprise normally not illuminating the material under inspection and illuminating or flashing an area of the machine conveyed material under inspection when the defect is detected at the indicator position.

7. The visual direct material defect position indication system for conveyed material inspection in claim 6, wherein said one or more material inspection devices comprise a pinhole detector, a machine vision and combinations thereof, wherein said one or more visual indicators are incorporated into said one or more material inspection devices.

8. The visual direct material defect position indication system for conveyed material inspection in claim 6, wherein the one or more visual indicators comprise normally illuminating the machine conveyed material under inspection with one color and changing to another color of illumination for an area of the machine conveyed material under inspection when the defect is detected at the position of the correlated visual indicator.

9. The visual direct material defect position indication system for conveyed material inspection in claim 6, wherein the one or more visual indicators comprising a different color, colors, flashing and combinations thereof to indicate an area of the machine conveyed material not under inspection.

10. The visual direct material defect position indication system for conveyed material inspection in claim 6, wherein the one or more visual indicators that illuminate the material under inspection are comprised of one or more LED, LASER, incandescent, fluorescent and combinations thereof light emitting devices.

11. A visual combination direct and indirect material defect position indication system for conveyed material inspection, comprising:
  one or more visual indicators, said one or more visual indicators comprising one or more light sources;
  one or more material inspection devices designed to inspect machine conveyed material on a structure for defect position information of said machine conveyed material and actuate the correlated visual indicator of the one or more visual indicators with a position of a defect of the machine conveyed material based on the detect position information, said one or more material inspection devices designed to inspect for defects in said machine conveyed material, said machine conveyed material comprising formed, flat and combinations thereof of foil film, sheet and combinations thereof;
  said structure designed to span the width of and position the one or more visual indicators in proximity to the machine conveyed material under inspection;
  the proximity and position of one or more visual indicators designed to be correlated with the position of the defect in the machine conveyed material under inspection;
  said one or more visual indicators designed to visually indicate the defect in the machine conveyed material under inspection location relative to the structure and designed to indicate the location on the machine conveyed material under inspection;
  the one or more visual indicators designed to actuate by illuminating, not illuminating and combinations thereof;
  wherein the one or more visual indicators comprise being normally illuminated and the correlated visual indicator being turned off or flashed when the defect of said machine conveyed material is detected at the position of the correlated visual indicator,
or alternatively wherein the one or more visual indicators comprise being normally off and the correlated visual indicator being illuminated or flashed when the defect of said machine conveyed material is detected at the position of the correlated visual indicator.

12. The visual combination direct and indirect material defect position indication system for conveyed material inspection in claim 11, wherein said one or more material inspection devices comprise a pinhole detector, a machine vision and combinations thereof, wherein said one or more visual indicators are incorporated into said one or more material inspection devices.

13. The visual combination direct and indirect material defect position indication system for conveyed material inspection in claim 11, wherein the one or more visual indicators comprise being one color when the defect is not detected and changing to a different color when the defect is detected at the position of the correlated visual indicator.

14. The visual combination direct and indirect material defect position indication system for conveyed material inspection in claim 11, wherein the one or more visual indicators comprise a different color, colors, flashing and combinations thereof to indicate an area of the conveyed machine material not under inspection.

15. The visual combination direct and indirect material defect position indication system for conveyed material inspection in claim 11, wherein the one or more visual indicators that illuminate the conveyed machine material under inspection are comprised of one or more LED, LASER, incandescent, fluorescent and combinations thereof light emitting devices.

16. The visual combination direct and indirect material defect position indication system for conveyed material inspection in claim 11, wherein each visual indicator is operable to both indicate the correlated position of the defect of the conveyed machined material on the structure and project light onto the conveyed machined material to indicate the position of the defect.

* * * * *